United States Patent [19]

Grandvallet et al.

[11] Patent Number: 5,023,389

[45] Date of Patent: Jun. 11, 1991

[54] PROCESS FOR PREPARING NORMALLY LIQUID OXYGENATE AND HYDROCARBONACEOUS PRODUCTS FROM A HYDROCARBON FEED CONTAINING LINEAR- AND BRANCHED OLEFINS

[75] Inventors: Pierre Grandvallet; Andras Guus Theodorus George Kortbeek; Johannes Petrus Van Den Berg; Karl-Heinz Röbschläger, all of Amsterdam, Netherlands

[73] Assignee: Shell Oil Company, Houston, Tex.

[21] Appl. No.: 308,489

[22] Filed: Feb. 10, 1989

[30] Foreign Application Priority Data

Feb. 22, 1988 [GB] United Kingdom ............... 8804033

[51] Int. Cl.[5] ........................................ C07C 2/00
[52] U.S. Cl. .................................. 585/304; 585/314; 585/315; 585/322; 585/323; 585/329; 585/331; 585/332
[58] Field of Search .............. 585/304, 322, 323, 329, 585/331, 332, 864, 518, 519, 531, 533, 314

[56] References Cited

U.S. PATENT DOCUMENTS

| | | | |
|---|---|---|---|
| 3,402,217 | 9/1968 | Engelbrecht et al. | 260/683.15 |
| 3,644,565 | 2/1972 | Biale | 260/683.43 |
| 4,218,569 | 8/1980 | Chase et al. | 585/519 |
| 4,454,367 | 6/1984 | Sakurada et al. | 585/533 |
| 4,517,396 | 5/1985 | Hoek et al. | 585/533 |
| 4,520,225 | 5/1985 | Marty et al. | 585/519 |
| 4,528,411 | 7/1985 | Hutson, Jr. | 585/329 |
| 4,542,251 | 9/1985 | Miller | 585/533 |
| 4,544,791 | 10/1985 | Juguin et al. | 585/533 |
| 4,855,528 | 8/1989 | Young et al. | 585/533 |

FOREIGN PATENT DOCUMENTS

| | | | |
|---|---|---|---|
| 0281208 | 9/1988 | European Pat. Off. | |
| 0332243 | 9/1989 | European Pat. Off. | 585/519 |

*Primary Examiner*—Asok Pal
*Attorney, Agent, or Firm*—Ronald R. Reper

[57] ABSTRACT

The invention relates to a process for preparing normally liquid hydrocarbon products such as middle distillates and methyl-t-butylether from a hydrocarbon feed containing linear and branched olefins (e.g. propane and butenes in light ends) comprising at least the following steps:

i) selectively converting branched olefins in the feed in the presence of a catalyst into a normally liquid hydrocarbonaceous product (e.g. MTBE);

ii) separating linear olefins from product obtained in step (i), and iii) catalytically oligomerizing linear olefins obtained from step (ii) into liquid hydrocarbons such as middle distillates.

8 Claims, 2 Drawing Sheets

PROCESS FOR PREPARING NORMALLY LIQUID OXYGENATE AND HYDROCARBONACEOUS PRODUCTS FROM A HYDROCARBON FEED CONTAINING LINEAR- AND BRANCHED OLEFINS

BACKGROUND OF THE INVENTION

The invention relates to a process for preparing normally liquid hydrocarbonaceous products from a hydrocarbon feed containing linear- and branched olefins.

A variety of one—and multistep—processes is known for the preparation of hydrocarbonaceous products such as oxygenates, middle distillates, alkylates and gasoline from an olefinic feed containing e.g. propene and/or butenes. These known processes have a number of draw-backs, however. One-step processes don't provide the flexibility to prepare a number of different products starting from a multi-component feed, whereas multi-step processes in many cases require splitting-up of such a feed in order to convert each component under optimal conditions.

In particular with the oligomerization of olefinic feed mixtures in the presence of solid catalysts it has been observed that the quality of the liquid hydrocarbon products (e.g. the cetane number of the gas oil fraction) is lower than when an olefinic feed substantially comprising linear olefins is processed.

Surprisingly, it has now been found that by first selectively converting branched olefins present in a feed mixture, followed by product separation and oligomerization of the linear olefins, excellent liquid hydrocarbon oligomerization products can be obtained in addition to valuable conversion products from the branched olefins.

SUMMARY OF THE INVENTION

The invention therefore relates to a process for preparing normally liquid hydrocarbonaceous products from a hydrocarbon feed containing linear- and branched olefins which comprises the following steps:
i) selectively converting branched olefins in the feed in the presence of a catalyst into a normally liquid hydrocarbonaceous product;
ii) separating linear olefins from product obtained in step (i), and
iii) oligomerizing linear olefins obtained from step (ii) in the presence of a solid catalyst into liquid hydrocarbons.

DESCRIPTION OF PREFERRED EMBODIMENTS

Figure 1:
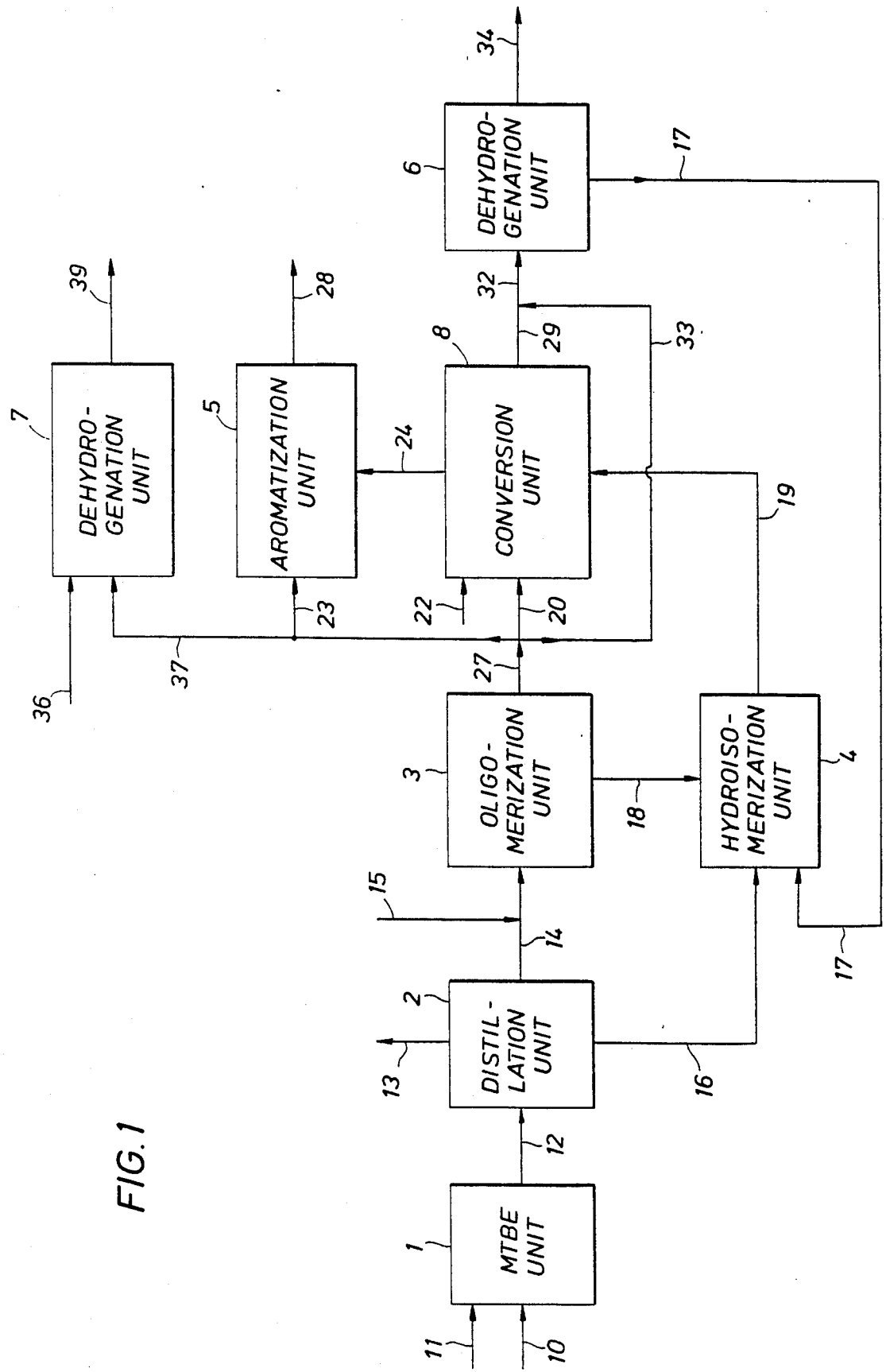
FIG. 1 schematically represents a flow diagram of a preferred embodiment of the invention.

Monoolefins are preferably used as feed (components). The olefins preferably have at most six carbon atoms per molecule ($C_6^-$ olefins); preferably, the olefins employed as feed for at least one of the steps (i) and (iii) contain compounds having 3 and 4 carbon atoms i.e. propene and in addition 1-butene and/or 2-butene as linear olefin, and 2-methyl propene as branched olefin.

In addition, the hydrocarbon feed to step (i) suitably contains (cyclic) paraffins, in particular from 10 to 70% by weight.

Furthermore, the hydrocarbon feed may contain di-olefins and mono-olefins having more than six carbon atoms per molecule and/or aromatic compounds.

The hydrocarbon feed is suitably obtained as by-product from (fluid) catalytic cracking processes, thermal cracking processes (e.g. for the preparation of ethene), coking- and/or pyrolysis processes.

Suitable feeds for the present process can also be prepared starting from synthesis gas which is first converted into methanol and subsequently into a product substantially consisting of $C_6^-$ olefins. Alternatively, the synthesis gas can be converted in the presence of a Fischer-Tropsch type of catalyst into a product which in addition to paraffinic hydrocarbons contains a considerable amount of $C_6^-$ olefins.

In a preferred embodiment of the process according to the invention in step (i) the branched feed olefin 2-methyl propene is converted with methanol (which may have been prepared starting from synthesis gas as described hereinbefore) in the presence of an acid-type catalyst into 2-methoxy-, 2-methyl propane (commonly described as methyl-t-butylether i.e. MTBE). It appears that by means of such an etherification process branched olefins are selectively removed from a hydrocarbon feed mixture which also contains linear olefins and, optionally, paraffins. Even when a complete light ends fraction containing olefins and paraffins having 3-6 carbon atoms per molecule is employed as feed for MTBE preparation in step (i) of the present process, the resulting product stream is well suited for the next steps of the process due to the selective removal of branched olefins from said stream.

The conversion of branched olefins in step (i) is suitably performed in the presence of an acidic catalyst, i.e. having acid properties, e.g. such as an inorganic acid (e.g. phosphoric acid or sulphuric acid) on a refractory oxide carrier (e.g. silica and/or alumina), a crystalline (alumina) silicate in the hydrogen form or a strongly acidic microporous organic ion exchange resin. Suitable temperatures for carrying out the conversion in step (i) are from 0° to 200° C., and in particular from 10° to 100° C. Suitable pressures are from 1 to 100 bar, in particular from 1-20 bar. The space velocity in the conversion zone(s) employed in step (i) is suitably from 0.1 to 10 kg hydrocarbon feed/kg catalyst.hour, and in particular from 0.2 to 5 kg feed/kg catalyst.hour.

For the preparation of MTBE, methanol and 2-methyl propene are suitably reacted in step (i) in a molar ratio of 1.5:1 to 5:1, and preferably from 2:1 to 4:1.

In an alternative embodiment of the process according to the invention branched olefins are removed in step (i) by means of polymerization in the presence of an acid-type catalyst which may be similar to those described hereinbefore for the preparation of MTBE under similar reaction conditions without addition of methanol to the conversion zone of step (i).

Whereas MTBE is a well known octane booster for motor gasoline, the gasoline fraction of a polymerization product alternatively, or even simultaneously, prepared in step (i) of the present process has itself a high octane rating and can be a useful blending component for the gasoline pool in a refinery.

Furthermore, it is envisaged to prepare 2-hydroxy, 2-methyl propane (t-butyl alcohol) in step (i) of the present process, again employing an acid-type catalyst (preferably immobilized on a carrier) in the presence of water.

Provided that paraffinic hydrocarbons are present in the feed to step (i), it is preferred to separate at least part of the paraffins in step (ii) from the linear olefins and from the conversion product(s) of branched olefins obtained from step (i) e.g. by means of distillation or molecular sieves, in order to avoid the presence of large quantities of paraffins in the feed stream to the oligomerization step (iii) of the present process. Moreover, the paraffins thus obtained can be suitably used as feed for additional process steps which will be discussed hereinafter.

The solid catalyst employed in step (iii) of the process according to the invention preferably comprises at least one metal (Z) selected from the group consisting of metals from Groups 1b, 2a, 2b, 3a, 4b, 5b, 6b and 8 of the Periodic Table of the Elements and a crystalline trivalent metal (Q) silicate).

Reference is made to the Periodic Table of the Elements as published in the "Handbook of Chemistry and Physics", 55th Edition (1975), CRC Press, Ohio, USA.

Preferably, at least part of the amount, and most preferably the total amount, of metal(s) Z has(have) been incorporated into the catalyst by means of ion exchange. Preferably, the catalyst applied in step (iii) of the process according to the invention is prepared by using a mordenite-type of carrier material, which comprises exchangeable cations such as alkali metal-, hydrogen- and/or preferably ammonium ions. The carrier material is suitably treated one or more times with a solution of at least one metal salt such as an aqueous solution of a metal nitrate or -acetate. The ion exchange treatment is suitably carried out at a temperature from 0° C. up to the boiling temperature of the solution, and preferably at a temperature from 20°–100° C.

The valency n of the metals Z can vary from +1 to +6. Preferably, however, at least one of the metals Z in the second stage catalyst is bivalent or trivalent, in which case the molar ratio Z:Q is preferably greater than 0.5. Z is preferably selected from the group consisting of the bivalent metals copper, zinc, cadmium, magnesium, calcium, strontium, barium, titanium, vanadium, chromium, manganese, iron, cobalt and nickel. A particularly preferred metal Z is nickel.

The trivalent metal Q which is present in the crystal structure of the mordenite-type of metal silicate catalyst carrier used at least in step (iii) preferably comprises at least one metal selected from the group consisting of aluminium, iron, gallium, rhodium, chromium and scandium. Most preferably Q consists substantially of aluminium; the resulting crystalline aluminium silicate preferably comprises a major part of mordenite and most preferably consists substantially completely of mordenite.

The molar ratio silicon:Q in the catalyst is suitably in the range from 5:1 to 100:1 and preferably in the range from 7:1 to 30:1. This ratio is in most cases substantially identical to the molar ratio Si:Q in the crystalline metal silicate employed as carrier material, except when some of the metal Q has been removed from the crystal structure during the catalyst preparation e.g. by means of acid leaching.

If desired (e.g. in order to increase the crushing strength of the catalyst particles), the carrier material and/or the ready catalyst for either one of the steps of the present process can be combined with a binder material such as (a combination of) refractory oxide(s), clay and/or carbon. Suitable refractory oxides comprise alumina, silica, magnesia, zirconia, titania and combinations thereof.

The molar ratio Z:Q in the ready catalyst is preferably from 0.6–1.5 and most preferably from 0.2–1.2. A molar ratio Z:Q of 0.5 or less for bivalent metals Z results in a catalyst which is in some cases less stable than a catalyst for which said ratio is greater than 0.5. A very high molar ratio Z:Q of e.g. more than 2 could lead to difficulties in the catalyst preparation and result in a relatively inactive catalyst with a relatively low surface are a and pore volume due to the very high degree of loading with metal(s) Z.

In an alternative preferred embodiment of the process according to the invention the metal Z is identical with the metal Q and is incorporated in the crystal structure of the silicate; most preferably gallium is the metal Q in case no additional metal Z is present in the catalyst because it appears that the selectivity such a catalyst shows for the preparation of lubricating base oils is surprisingly high.

After loading of the carrier material with the metal(s) Z, the catalytically active composition thus obtained is preferably dried and calcined before being employed as catalyst in the process according to the present invention. Drying is suitably carried out at a temperature from 100°–400° C., and preferably from 110°–300° C., for a period of 1–24 hours; the calcination temperature is suitably from 400°–800° C. and preferably from 450°–650° C. The calcination treatment is suitably carried out at (sub-)atmospheric or elevated pressure for a period of 0.1–24 hours, and preferably of 0.5–5 hours in air or in an inert (e.g. nitrogen) atmosphere.

The process according to the invention can be carried out in one or more fixed-, moving- and/or fluidized beds or in a slurry-type of reactor; preferably, the process is carried out in a fixed bed of catalyst particles such as extrudates, pellets or spheres passing sieve openings having a width from 0.05–5 mm, and preferably from 0.1–1 mm.

Step (iii) of the present process is suitably operated at a temperature which is at least 100° C. above the operating temperature in step (i), in particular when the latter temperature is from 10°–100 ° C. as discussed hereinbefore.

Step (iii) is preferably carried out at a temperature from 150°–330° C., a pressure from 1–100 bar and a space velocity from 0.1–10 kg olefins feed/kg catalyst.-hour. Most preferably, step (iii) is carried out at a temperature from 180°–300° C., a pressure from 10–50 bar and a space velocity from 0.2–5 kg olefin feed/kg catalyst hour.

Various preferred embodiments of the process according to the invention will be discussed with the use of FIGS. 1 and 2 in which similar process steps and -streams have been indicated with the same reference numerals.

Figure 2:
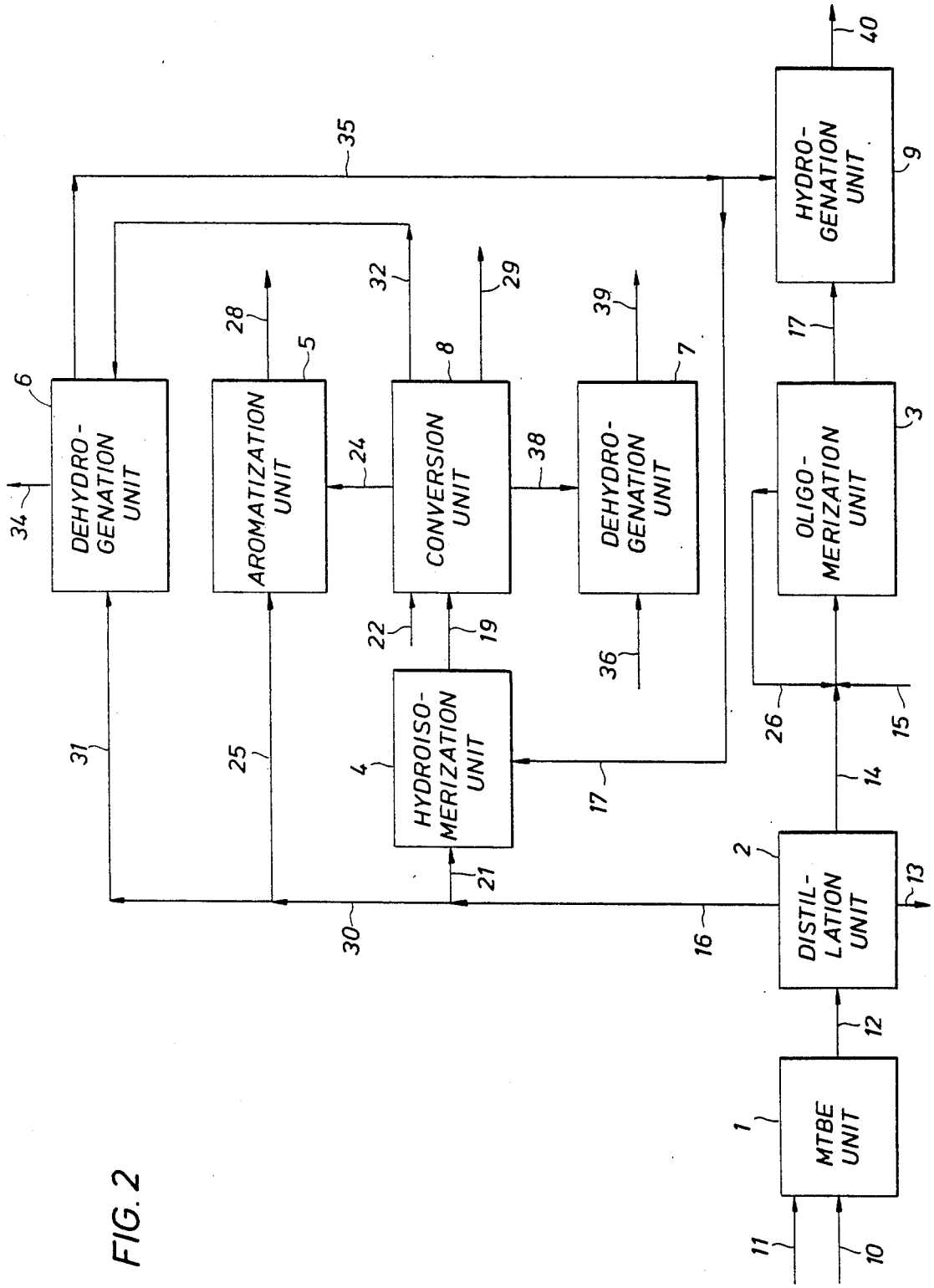
FIG. 2 schematically represents a flow diagram of yet another preferred embodiment of the invention.

Common to both FIGS. 1 and 2 are essential process steps (i), (ii) and (iii), which are schematically represented by units (1), (2) and (3), respectively.

In FIG. 1 a feed stream (10), containing at least a quantity of linear- and branched olefins, in particular linear butene(s) and 2-methylpropene, and in addition paraffins, and methanol stream (11) are converted in MTBE unit (1) into MTBE. Product stream 12 contains, in addition to MTBE, substantially unconverted paraffins and linear olefins.

From separation unit (2) (e.g. one or more distillation columns) MTBE is obtained through line (13), in some cases together with unconverted methanol and methoxy methane as byproduct. Stream (14) containing linear olefins (such as 1-butene, 2-butene, optionally propene) and linear- and branched paraffins (such as n-butane and 2-methyl butane, and optionally propane) is directed to oligomerization unit (3).

In case a $C_3/C_4$ feed for the process according to the invention is available as separate $C_3$- and $C_4$- fractions, it is preferred to introduce the $C_4$-fraction (which may also contain small amounts of $C_3$) through line (10) and the $C_3$-fraction through line (15) in order to keep the dimensions of unit (1) as small as possible and avoid undesired side reactions with the $C_3$-fraction.

Optionally, paraffins are obtained as a separate stream (16) from unit (2) which is directed to hydroisomerization unit (4) (step (iv) of the present process) wherein linear paraffins (e.g. n-butane) are catalytically hydroisomerized in the presence of hydrogen (supplied through line (17)). It is furthermore possible to employ in unit (4) a paraffin stream (18) (e.g. containing propane and/or n-butane) obtained from unit (3). The hydroisomerization step (iv) is suitably carried out in the presence of a catalyst comprising at least one hydrogenating metal and a moderately acidic carrier; a preferred catalyst comprises a Group 8 metal (in particular platinum and/or palladium) on a microporous crystalline silicate (in particular mordenite with a surface area from 100 to 800 $m^2/g$).

Suitable hydroisomerization conditions include a temperature from 100° to 400° C., a pressure from 1-100 bar and a space velocity from 0.1 to 10 kg hydrocarbon feed/kg catalyst hour. Preferred conditions are a temperature from 150° to 300° C., a pressure from 10 to 40 bar and a space velocity from 0.5 to 5 kg feed/kg catalyst hour.

In a preferred embodiment of the process according to the invention in unit (8) at least one of the paraffin containing streams (19) (containing 2-methyl propane obtained from step (iv)), (20) (obtained from step (iii)) and (21) (obtained from step (ii)) are converted in the presence of olefins having at least 3 carbon atoms per molecule ($C_3+$) (supplied separately through line (22) if not already present in streams (19), (20) and (21). The $C_3+$ olefins-containing stream (22) is suitably obtained from the same source as stream (15); alternatively, $C_3+$ olefins obtained from the Shell Middle Distillate Synthesis (SMDS) process or from catalytic conversions of oxygenated hydrocarbons (such as methanol) can be used as feed for unit (8).

Said conversion (step (a)) is carried out in the presence of an acid-type catalyst, resulting in alkylated (i.e branched) hydrocarbons (stream 29) having at least 7 carbon atoms per molecule which are excellent for use as motor gasoline (component). The alkylation catalyst is suitably hydrofluoric acid or sulphuric acid.

Suitable alkylation conditions are a temperature from 0° C. to 65° C., a pressure from 2 to 15 bar and a space velocity from 0.05 to 1 vol. hydrocarbon feed/vol. acid catalyst hour. Preferred conditions are a temperature from 5° C. to 40° C., a pressure from 5 to 10 bar and a space velocity from 0.1 to 0.6 vol feed/vol. acid catalyst hour.

According to a further preferred embodiment of the present process paraffins obtained from at least one of the steps (ii), (iii) and (a) (i.e. obtained from units (2), (3) and (8), respectively) are converted in step (b) into aromatic-rich gasoline (stream 28) in the presence of a catalyst containing at least one of the metals zinc, gallium and thorium, and a crystalline silicate. Step (b) is carried out in unit (5) as schematically depicted in FIGS. 1 and 2 which unit is supplied through lines (23), (24) and/or (25) with paraffins comprising at least propane, n-butane and/or 2-methyl propane.

A preferred catalyst for step (b) comprises a crystalline gallium silicate (in particular with a MFI-type of structure) which may optionally be combined with zinc; suitable temperatures for carrying out step (b) with such a catalyst are from 400° to 600° C., in particular from 500° to 600° C. Suitable reaction conditions for step (b) using a catalyst without gallium in the crystal structure are a temperature from 200°-600° C., a pressure from 1-100 bar and a space velocity from 0.1-10 kg paraffin feed/kg catalyst hour.

Said crystalline gallium silicate catalyst can also advantageously be applied in essential step (iii) of the process according to the invention to produce middle distillates (i.e. kerosine and gas oil) and/or lubricating base oil fractions (stream 27) with excellent properties and having a high added value compared with a gasoline fraction which can also be prepared in unit (3); a gasoline stream is suitably recycled via line (26) (see FIG. 2) in order to maximize the production of higher-boiling fractions.

When a crystalline gallium silicate is used in unit (3), a moderate reaction temperature from 180°−240° C. is preferably maintained in order to minimize aromatics formation and enhance the production of lubricating base oil fractions.

Hydrogen obtained as by-product from unit (5) during the preparation of aromatic-rich gasoline can be suitably employed for a selective pre-hydrogenation of dienes (not shown in the Figures) which may be present in feed stream (10) or for hydrofinishing oligomerized product stream (27) in hydrogenation unit (9) (from which hydrofinished products are obtained via line (40)).

In yet another preferred embodiment of the process according to the invention unconverted paraffins such as propane, n-butane and/or 2-methyl propane are catalytically and/or thermally dehydrogenated in unit (6). The paraffins can be obtained either directly from separation unit (2) via lines (30) and (31), from aromatic gasoline unit (8) through line (32), and/or from oligomerization unit (3) directly via line (33).

The olefins obtained from unit (6) through line (34) are suitably recycled (not depicted in the Figures) to unit (1) and/or unit (3).

The hydrogen produced in unit (6) is suitably directed via line (17) to hydroisomerization unit (4) or via line (35) to hydrogenation unit (9).

Thermal dehydrogenation is suitably carried out at a temperature from 1000° to 1600° C., and preferably from 1100°−1400 ° C. Catalytic dehydrogenation is suitably carried out at a temperature from 300° to 1000° C., and preferably from 400° to 700° C. in the presence of a catalyst comprising a metal or metal compound(s) (e.g. $Cr_2O_3/ZnO$) having dehydrogenation capability on a refractory carrier material such as nickel on silica, alumina or a combination thereof as carrier.

Dehydrogenation in unit (6) is suitably carried out at a pressure from 0.1 to 10 bar, and preferably from 0.2 to 5 bar. The space velocity in unit (6) is suitably from 0.1 to 10 kg paraffin feed/kg catalyst hour and preferably from 0.2 to 5 kg paraffins feed/kg catalyst hour.

Paraffins obtained from at least one of the steps (ii), (iii), (iv) and (a) (carried out in units (2), (3), (4) and (8)) are dehydrogenated in unit (7) in the presence of steam supplied through line (36) in an alternative preferred embodiment of the process according to the invention. Paraffins such as propane, n-butane and/or 2-methyl propane are supplied via line (37) or (38) to unit (7) and products are removed via line (39).

Steam cracking conditions in unit (7) are suitably a temperature from 600° to 1400° C., a pressure from 1 to 10 bar, a residence time from 0.5 to 1.5 s, and a steam/paraffin weight ratio of 0.1 to 1.0.

Preferred stream cracking conditions are a temperature from 700° to 900° C., a pressure from 1.5 to 5 bar, a residence time from 0.1 to 1 s and a steam/paraffin weight ratio of 0.2 to 0.7.

Olefins obtained from unit (7) through line (39) are suitably recycled (after separation from steam; not depicted in the Figures) to unit (1) and/or unit (3), or used as feedstock for manufacturing chemicals.

The invention furthermore relates to liquid hydrocarbons and oxygenates prepared by a process as described hereinbefore. Such normally liquid hydrocarbons include products boiling in the gasoline range (40°-150° C.), the middle distillate range (kerosene- and gas oil fractions boiling from 150°-370° C.) and in the lubricating base oil range (boiling above 370° C.); the oxygenates include ethers, in particular MTBE (methyl-t.butylether) and alcohols, in particular 2-hydroxy, 2-methyl propane.

We claim:

1. A process for preparing normally liquid oxygenate and hydrocarbonaceous products from a hydrocarbon feed containing 10-70% by weight paraffins, linear and branched olefins having 3 and 4 carbon atoms including 2-methyl-propene, and having at most 6 carbon atoms per molecule which process comprises the following steps:
   i) selectively converting branched olefins in the feed with methanol in the presence of a catalyst into a normally liquid oxygenated product;
   ii) separating product obtained in step (i) by distillation or contact with molecular sieves to obtain a linear olefins-containing stream and a stream of paraffins,
   iii) oligomerizing linear olefins in said linear olefins-containing stream from step (ii) in the presence of a solid catalyst into liquid hydrocarbons,
   iv) feeding said stream of paraffin from step (ii) to a hydroisomerization unit together with hydrogen, and catalytically hydroisomerizing linear paraffins in said second stream to obtain a product stream having a higher branched paraffin content than said feed, and,
   having an additional step (a) comprising feeding at least one of said stream of paraffins from step (ii), and said product stream from step (iv) to a conversion unit together with olefins having at least 3 carbon atoms per molecule and converting said feed in the presence of an acidic catalyst into an alkylated hydrocarbon product stream.

2. Process according to claim 1 wherein the solid catalyst employed in step (iii) essentially consists of at least one metal (Z) selected from the group consisting of metals from Groups 1b, 2a, 2b, 3a, 4b, 5b, 6b and 8, and a crystalline trivalent metal (Q) silicate.

3. Process according to claim 1 wherein step (ii) uses distillation of said product of step (i).

4. Process according to claim 1 wherein step (ii) uses contacting said product of step (i) with molecular sieves in a separation unit.

5. Process according to claim 1 having an additional step (b) comprising feeding at least one of said second stream of paraffins from step (ii), said products stream from step (iv), and said alklyated hydrocarbons product stream of step (a) and converting said feed at a temperature in the range from 400° to 600° C. in the presence of a catalyst containing at least one of the metals zinc, gallium, and thorium, and a crystalline silicate, to obtain an aromatic gasoline product stream.

6. Process according to claim 5 wherein said catalyst essentially consists of crystalline gallium silicate.

7. Process according to claim 1 having an additional step (c) comprising feeding at least one of said stream of paraffins from step (ii), said products stream from step (iv) and said alkylated products stream from step (a) to a dehydrogenation unit together with steam at steam cracking conditions to obtain an olefins-containing steeam-cracked product stream.

8. Process according to claim 1 having an additional step (d) comprising feeding at least one of said stream of paraffins from step (ii), said products stream from step (iv), and said alkylated products stream from step (a) to a dehydrogenation unit wherein said feed is dehydrogenated either thermally at a temperature from 1000° to 1600° C., or catalytically at a temperature from 300° to 1000° C. in the presence of a catalyst comprising $Cr_2O_3/ZnO_2$ or nickel on a refractory carrier material, to obtain a hydrogen product stream and an olefinic hydrocarbon product stream, and passing said hydrogen product stream to said hydroisomerization unit of step (iv).

* * * * *